(12) United States Patent
Clementi et al.

(10) Patent No.: US 8,575,222 B2
(45) Date of Patent: Nov. 5, 2013

(54) USE OF NITROOXYDERIVATIVES OF DRUG FOR THE TREATMENT OF MUSCULAR DYSTROPHIES

(75) Inventors: Emilio Clementi, Milan (IT); Giulio Cossu, Milan (IT); Silvia Brunelli, Milan (IT); Ennio Ongini, Milan (IT)

(73) Assignee: Nicox S.A., Sophia Antipolis (FR)

( * ) Notice: Subject to any disclaimer, the term of this patent is extended or adjusted under 35 U.S.C. 154(b) by 37 days.

(21) Appl. No.: 12/159,577

(22) PCT Filed: Jan. 23, 2007

(86) PCT No.: PCT/EP2007/050630
§ 371 (c)(1),
(2), (4) Date: Aug. 5, 2008

(87) PCT Pub. No.: WO2007/088123
PCT Pub. Date: Aug. 9, 2007

(65) Prior Publication Data
US 2009/0093510 A1    Apr. 9, 2009

Related U.S. Application Data

(60) Provisional application No. 60/764,755, filed on Feb. 3, 2006.

(51) Int. Cl.
*A01N 33/18* (2006.01)
*A01N 33/24* (2006.01)
*A61K 31/04* (2006.01)
*C07C 201/00* (2006.01)
*C07C 205/00* (2006.01)

(52) U.S. Cl.
USPC .......................................... 514/740; 568/924

(58) Field of Classification Search
USPC ................. 514/509, 740; 558/480; 568/924
See application file for complete search history.

(56) References Cited

U.S. PATENT DOCUMENTS

| 5,545,614 A * | 8/1996 | Stamler et al. ............... 514/6 |
| 2005/0113409 A1 * | 5/2005 | Connor et al. ................ 514/311 |

FOREIGN PATENT DOCUMENTS

| EP | 1 473 288 A1 | 11/2004 |
| WO | WO 95/30641 A1 | 11/1995 |
| WO | WO 00/53191 A2 | 9/2000 |
| WO | WO 2004/105754 A1 | 12/2004 |
| WO | WO 2005/023305 A2 | 3/2005 |
| WO | WO 2006130982 A1 * | 12/2006 |
| WO | WO 2007/088050 | 8/2007 |

OTHER PUBLICATIONS

Mariotto et. al., British J. Pharmacology, 1995, Stockton Press, vol. 115, pp. 225-226.*
Naimi et. al., J. Med. Chem., 2003, American Chemical Society, vol. 46, pp. 995-1004.*
Burgaud, Drugs of the Future, 1999, Thomson Reuters, vol. 24, issue 8, pp. 858-861.*
Wehling M et al: "A nitric oxide synthase transgene ameliorates muscular dystrophy in mdx mice." The Journal of Cell Biology Oct. 1, 2001, vol. 155, No. 1, pp. 123-131, XP002433415; ISSN: 0021-9525; abstract; p. 123, col. 2, paragraph 2-p. 124, col. 1, paragraph 2.
Bredt D S: "No skeletal muscle derived relaxing factor in Duchenne muscular dystrophy." Proceedings of the National Academy of Sciences of the United States of America Dec. 8, 1998, vol. 95, No. 25, pp. 14592-14593, XP002433416; ISSN: 0027-8424 cited in the application abstract; p. 14593, col. 1.
Engvall Eva et al: "The new frontier in muscular dystrophy research: booster genes." The FASEB Journal: Official Publication of the Federation of American Societies for Experimental Biology Sep. 2003, vol. 17, No. 12, Sep. 2003, pp. 1579-1584, XP002433417 ISSN: 1530-6860 abstract; p. 1581, col. 2, paragraph 2.
Chiroli V et al: "Nitric oxide-donating non-steroidal anti-inflammatory drugs: The case of nitroderivatives of aspirin" European Journal of Medicinal Chemistry, Editions Scientifique Elsevier, Paris, FR, vol. 38, No. 4, Apr. 2003, pp. 441-446, XP004425019 ISSN: 0223-5234 abstract; p. 442, col. 1, paragraph 2; p. 442, col. 2, paragraphs 2,3; p. 445, col. 1, paragraph 5-col. 2.
Ongini Ennio et al: "Nitric oxide (NO)-releasing statin derivatives, a class of drugs showing enhanced antiproliferative and anti-inflammatory properties." Proceedings of the National Academy of Sciences of the United States of America Jun. 1, 2004, vol. 101, No. 22, Jun. 1, 2004, pp. 8497-8502, XP002433418 ISSN: 0027-8424, abstract; p. 8497, col. 1, paragraph 2-col. 2, paragraph 2, figure 1, p. 8501, col. 1, paragraph 2; p. 8502, col. 1, paragraph 1; p. 8502, col. 2, paragraph 2,3.
Jay E. Brenman et al., "Nitric Oxide Synthase Complexed with Dystrophin and Absent from Skeletal Muscle Sarcolemma in Duchenne Muscular Dystrophy," Cell, vol. 82, pp. 743-752, Sep. 8, 1995.
Wen-Jinn Chang et al., "Neuronal nitric oxide synthase and dystrophin-deficient muscular dystrophy,"Proc. Natl. Acad. Sci., vol. 93, pp. 9142-9147, Aug. 1996, Medical Sciences.
Zarko Grozdanovic et al., "Nitric oxide synthase I (NOS-I) is deficient in the sarcolemma of striated muscle fibers in patients with Duchenne muscular dystrophy, suggesting an association with dystrophin," Acta histochem. (Jena) 98, pp. 61-69 (1996), Gustav Fischer Verlag Jena—Stuttgart—New York.
Z. Grozdanovic et al., "Nitric oxide synthase in skeletal muscle fibers: a signaling component of the dystrophin-glycoprotein complex," Histol Histopathal (1999) 14, pp. 243-256.
Maria Julia Marques et al., "Muscle regeneration in dystrophic *mdx* mice is enhanced by isosorbide dinitrate," Neuroscience Letters 382 (2005) pp. 342-345.
Clara Sciorati et al., "Ex vivo treatment with nitric oxide increases mesoangioblast therapeutic efficacy in muscular dystrophy," Journal of Cell Science 119, pp. 5114-5123, The Company of Biologists 2006 doi:10.1242/jcs.03300.
Vincent Voisin et al., L-arginine improves dystrophic phenotype in *mdx* mice, Neurobiology of Disease 20 (2005) pp. 123-130.

* cited by examiner

*Primary Examiner* — Sreeni Padmanabhan
*Assistant Examiner* — Sarah Pihonak
(74) *Attorney, Agent, or Firm* — Arent Fox LLP

(57) ABSTRACT

The present invention relates to the use of nitric oxide releasing compounds for retarding or reversing muscular dystrophies such as Duchenne and Becker dystrophies.

17 Claims, No Drawings

USE OF NITROOXYDERIVATIVES OF DRUG FOR THE TREATMENT OF MUSCULAR DYSTROPHIES

CROSS-REFERENCED TO RELATED APPLICATION

This application is a National Stage entry of International Application No. PCT/EP2007/050630, filed Jan. 23, 2007, which claims priority to U.S. Provisional Application No. 60/764,755, filed Feb. 3, 2006, the disclosure of the prior applications are incorporated in its entirety by reference.

The present invention relates to the use of nitric oxide releasing compounds for retarding or reversing muscular dystrophies such as Duchenne and Becker dystrophies.

Muscular dystrophies are caused by progressive degeneration of skeletal muscle fibres. Lack of one of several proteins located either at the plasma membrane or within internal membranes, increases the probability of damage during contraction, and eventually leads to fibre degeneration, accompanied by severe local inflammation with infiltration of immune-competent cells.

Muscular dystrophies encompasse a group of inherited, progressive muscle disorders, distinguished clinically by the selective distribution of skeletal muscle weakness. The two most common forms of muscle dystrophy are Duchenne and Becker dystrophies, each resulting from the inheritance of a mutation in the dystrophin gene, which is located at the Xp21 locus. Other dystrophies include, but are not limited to, limb-girdle muscular dystrophy, fascioscapulohumeral (Landouzy-Dejerine) muscular dystrophy, congenital muscular dystrophy, myotonic dystrophy, and Emery-Dreifuss muscular dystrophy.

In the most severe form, such as Duchenne muscular dystrophy, regeneration is exhausted and skeletal muscle is progressively replaced by fat and fibrous tissue. This condition leads to patient showing a progressive weakness and eventually death by respiratory and/or cardiac failure.

The symptoms of Duchenne muscular dystrophy occur almost exclusively in males, and start at about 3-7 years of age with most patients confined to a wheelchair by 10-12 years and many die at about 20 years of age due to respiratory complications.

Of the different medications that have been tried as potential treatments for Duchenne muscular dystrophy, only the corticosteroids such as prednisone, prednisolone and deflazacort have shown potential for providing temporary improvement. This improvement results mainly from slowing the rate of progression or stabilizing muscle strength and function. Corticosteroid therapy also leads to side effects; as yet there is no consensus regarding their use as standard treatment.

Corticosteroids, such as prednisone, are believed to act by blocking the immune cell activation and infiltration which are precipitated by muscle fiber damage resulting from the disease.

The long-term therapies with corticosteroids as the remedy for muscular dystrophy, are associated with adverse effects such as osteoporosis, hypertension and Cushing syndrome, weight gain, cataracts, short stature, gastrointestinal symptoms, behavioural changes in case of the prednisolone and weight gain and cataracts as for deflazacort.

Bredt D. S. in Proc. Natl. Acad. Sci. USA 95 (1998), 14592-14593 reports that nitric oxide (NO) generated by muscular NO synthase, which is structurally and functionally linked to the dystrophin complex at the sarcolemma, partici-
pates to physiological development and function of skeletal muscle by regulating vasodilation and thus supply oxygen during exercise, by increasing glucose uptake in the myofibres and by regulating the enzymes activity relevant to cell energy metabolism.

EP 759899 describes nitrooxy derivative of NSAIDs. The pharmacological data reported in the document show that these compounds show a good anti-inflammatory, analgesic and antithrombotic activities and an increased gastric tolerability than the correspondent parent drug. The document does not report that these compounds are active for the treatment of muscular degenerative diseases.

WO 2004/105754 describes statins nitroderivatives, which exhibit strong anti-inflammatory, antithrombotic and anti-platelet activities. The document reports that the statins nitroderivatives can be used for treating or preventing cardiovascular diseases and peripheral vascular diseases and all disorders associated with endothelial dysfunctions such as vascular complications in diabetic patients and atherosclerosis. Also this document does not report that these compounds are active for the treatment of muscular degenerative diseases.

WO 00/53191 discloses the use of nitric oxide (NO), NO donors, inhibitor of NO activity or regulator of NO production for the treatment of muscle diseases which include Duchenne dystrophy, Becker dystrophy, limb-girdle muscular dystrophy, fascioscapulohumeral (Landouzy-Dejerine) muscular dystrophy, congenital muscular dystrophy, myotonic dystrophy, and Emery-Dreifuss muscular dystrophy.

In particular the document discloses the results of a study of mdx dystrophic mice treated with deflazacort, deflazacort plus L-NAME (a NOS enzymes inhibitor) or deflazacort plus L-arginine (a NO donor). In the experiment muscle tissues of tibialis anterior muscle and diaphragm were collected from the treated animal and the central nucleation index (CNI), which is a useful measure of muscle damage index, was assessed. The results show that the addition of the NO donor to deflazacort did not improve the status of muscles in mdx mice and that L-NAME augmented the beneficial effects of deflazacort only on diaphragm. The author concluded that the results show that L-NAME o other NOS inhibitors can be used for improve the effects of steroid when applied in situ.

Thus, there is a need to identify therapeutic agents which slow the muscle fibres damage and delay the onset of disability in patients with muscular dystrophies, but cause a lesser degree of skeletal muscle atrophy than current therapies.

Quite surprisingly and unexpectedly, it was found that nitric oxide releasing compounds of formula M-X—Y—$ONO_2$ wherein M is the residue of a therapeutic agent which is an NSAID or a statin are effective for retarding or reversing (treatment) muscular dystrophies. Moreover they have the advantage that they induce fewer adverse side effects, they are well tolerated by the patients and therefore they can be used in long term therapies.

It is an object of the present invention the use of nitric oxide releasing drugs of formula (Ia)

$$M\text{-}X\text{—}Y\text{—}ONO_2 \quad\quad\quad (Ia)$$

or enantiomers or diasteroisomers thereof for the treatment of muscular dystrophies, wherein in the general formula (Ia) M, X and Y have the following meanings:

M is the residue selected from:
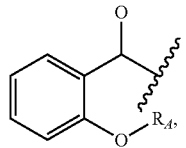
(I)
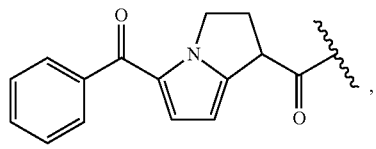
(II)
wherein $R_A$ is an hydrogen atom or —C(O)CH$_3$,
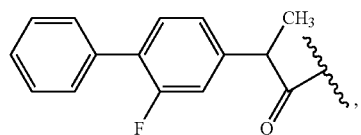
(III)
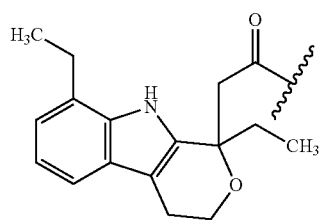
(IV)
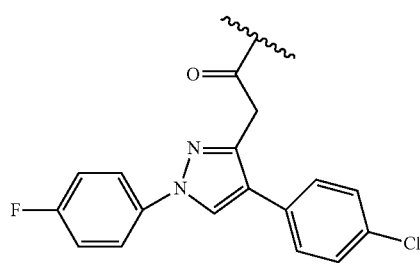
(V)
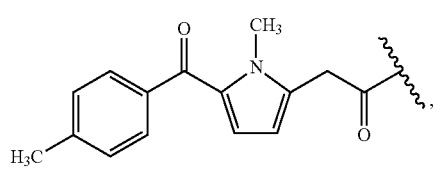
(VI)
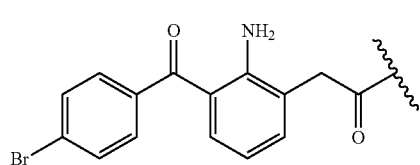
(VII)
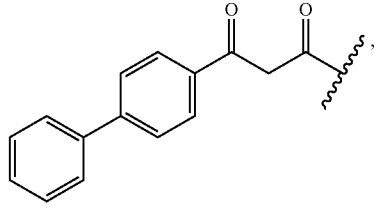
(VIII)
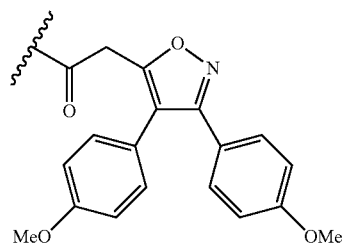
(IX)
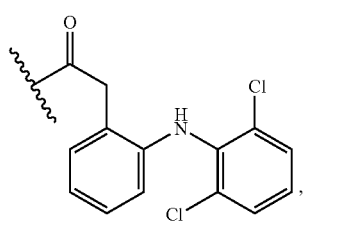
(X)
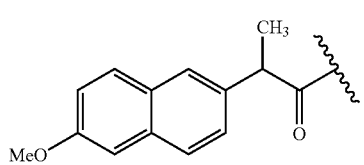
(XI)
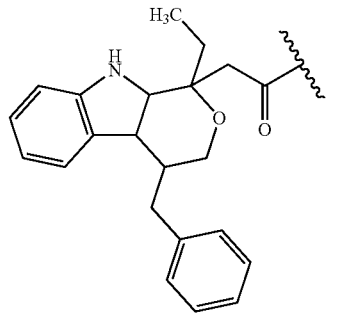
(XII)
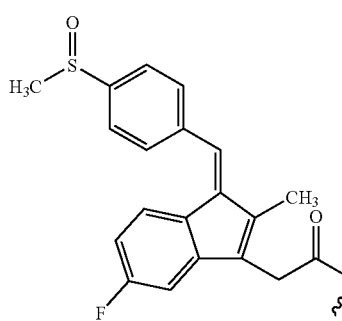
(XIII)

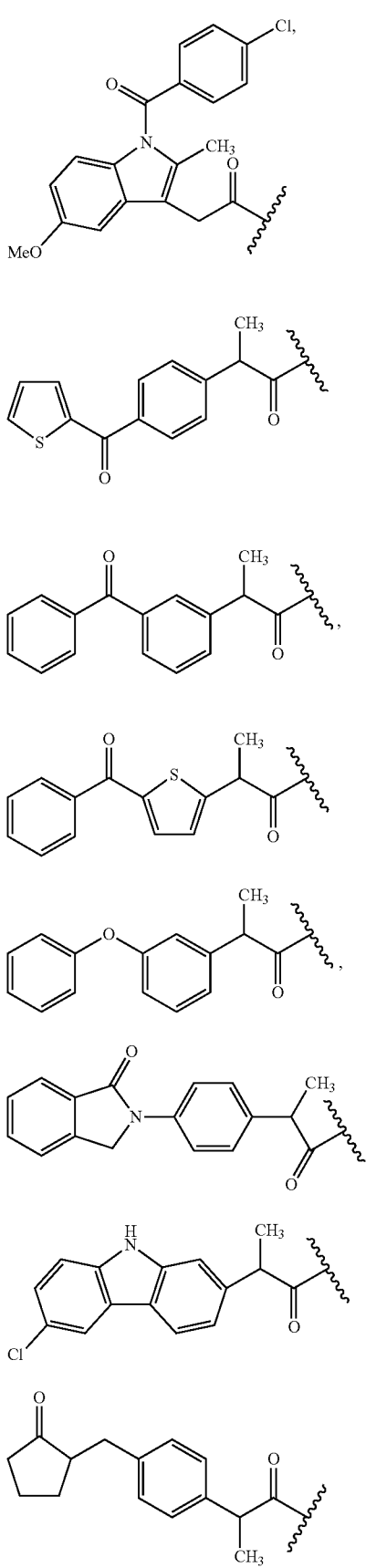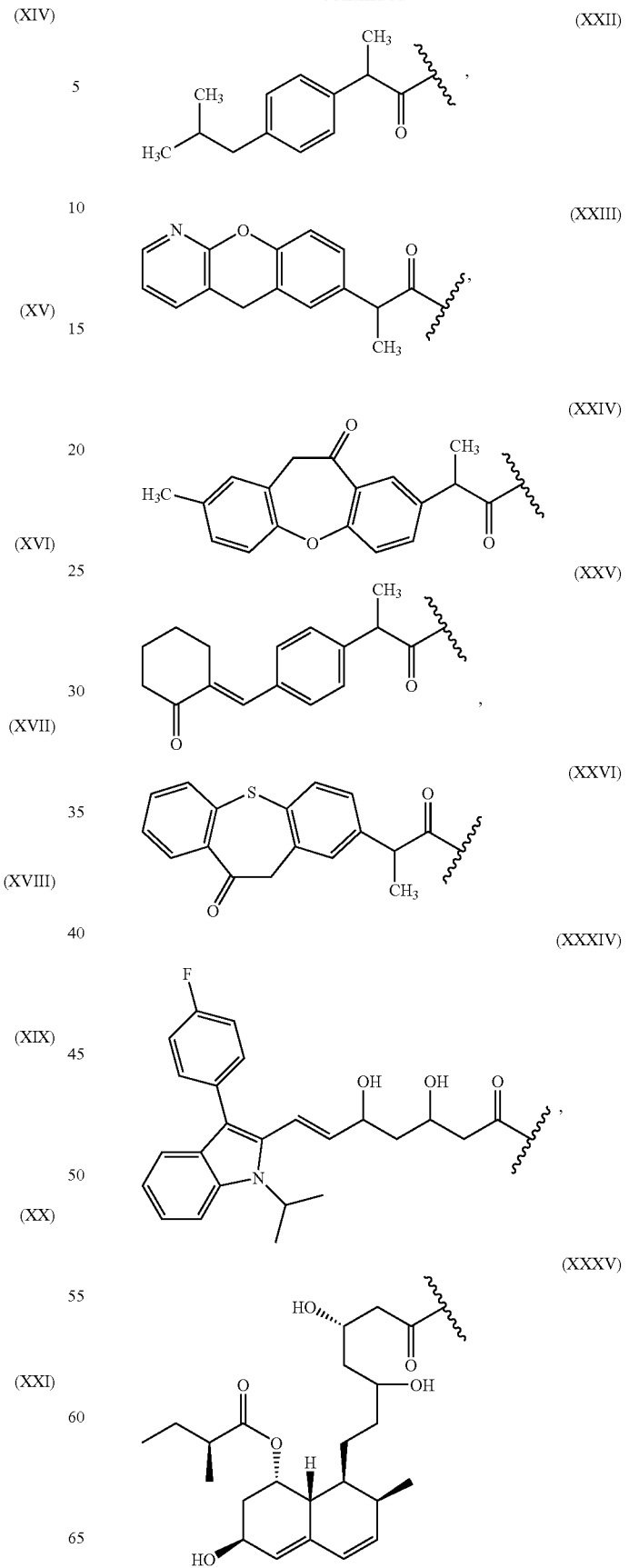

(XXXVI)

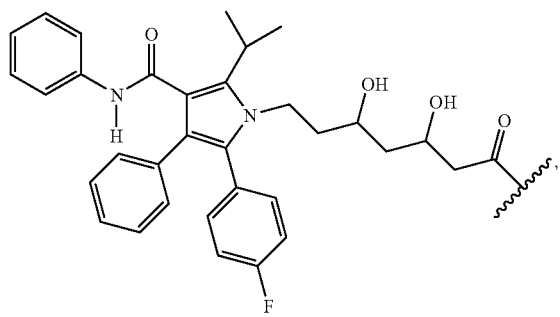

(XXXVII)

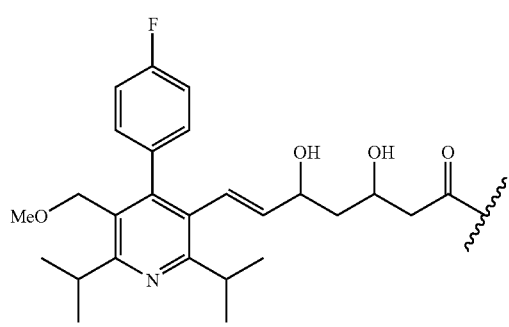

(XXXIX)

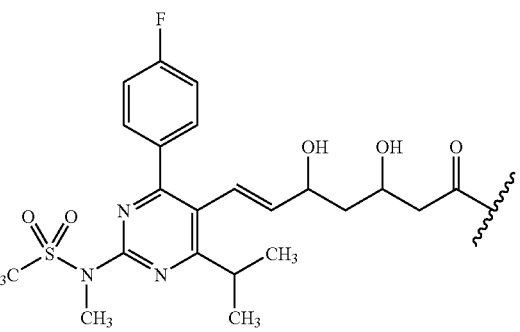

X is —O—, —S— or —NR¹—, wherein R¹ is H or linear or branched $C_1$-$C_6$ alkyl;

Y is a bivalent radical having the following meanings:

a)
straight or branched $C_1$-$C_{20}$ alkylene, preferably $C_1$-$C_{10}$, being optionally substituted with one or more of the substituents selected from the group consisting of: halogen atoms, hydroxy, —ONO₂ or T, wherein T is —OC(O) ($C_1$-$C_{10}$ alkyl)-ONO₂ or —O($C_1$-$C_{10}$ alkyl)-ONO₂; more preferably Y is $C_1$-$C_{10}$ alkylene;

$C_5$-$C_7$ cycloalkylene group optionally substituted with linear or branched $C_1$-$C_{10}$ alkyl group, preferably CH₃;

b)

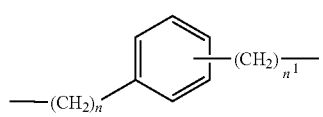

(XXVII)

c)

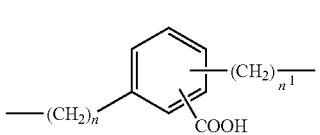

(XXVIII)

wherein n is an integer from 0 to 20, preferably n is an integer from 0 to 5, more preferably n is 0;

n¹ is an integer from 1 to 20, preferably n' is an integer from 1 to 5, more preferably n¹ is 1;

with the proviso that when Y is selected from the bivalent radicals mentioned under b) and c) then the —ONO₂ group of formula (I) is bound to —(CH₂)$_{n^1}$—;

d)

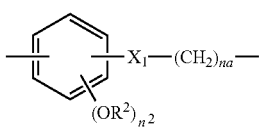

(XXIX)

wherein
$X_1$=—OCO— or —COO— and R² is H or CH₃;
na is an integer from 1 to 20; preferably [[n]] na is an integer from 1 to 5;
n² is an integer from 0 to 2;

e)

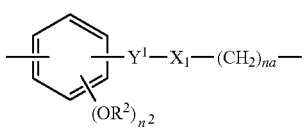

(XXX)

wherein:
Y¹ is —CH₂—CH₂— (CH₂)$_{n^2}$—; or —CH=CH— (CH₂)$_{n^2}$—;
$X_1$, na, n² and R² are as defined above;

f)

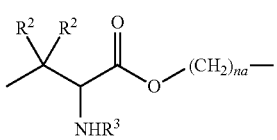

(XXXI)

wherein:
na and R² are as defined above, R³ is H or —COCH₃; with the proviso that when Y is selected from the bivalent radicals mentioned under d)-f) then the —ONO₂ group of formula (I) is bound to —(CH₂)$_{na}$;

with the proviso that when X is —NR¹—, wherein R¹ is as above defined Y cannot be f);

g)

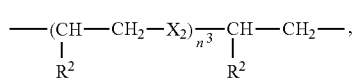 (XXXII)

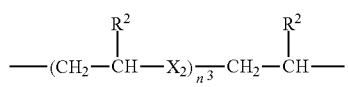 (XXXIII)

wherein
$X_2$ is —O— or —S—;
$n^3$ is an integer from 1 to 6, preferably from 1 to 4, and
$R^2$ is as defined above.

One preferred embodiment of the invention comprises the use of the nitric oxide releasing drug of formula (Ib)

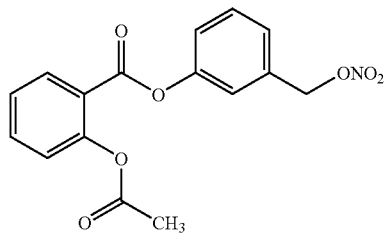 (Ib)

for the treatment of muscular dystrophies; the compound of formula (Ib) is known as 2-(acetyloxy)benzoic acid 3-(nitrooxymethyl)phenyl ester of formula.

Another preferred embodiment of the invention comprises the use of the nitric oxide releasing drug of formula (IIIb) or its enantiomers

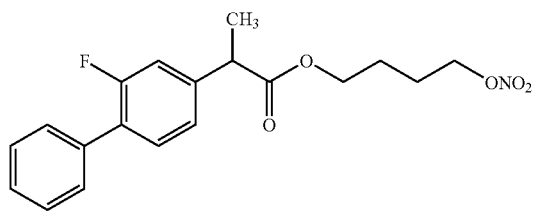 (IIIb)

for the retarding or reversing muscular dystrophies; the compound of formula (IIIb) is known as 2-fluoro-alfa-methyl-4 [1,1'-biphenyl]-4-acetic acid 4-nitrooxybutyl ester.

Another preferred embodiment of the invention comprises the use of a nitric oxide-releasing drug of formula (Ia) for treatment of muscular dystrophies, wherein in formula (Ia) M is selected from the group consisting of:

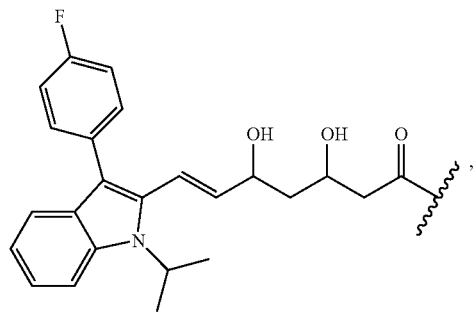 (XXXIV)

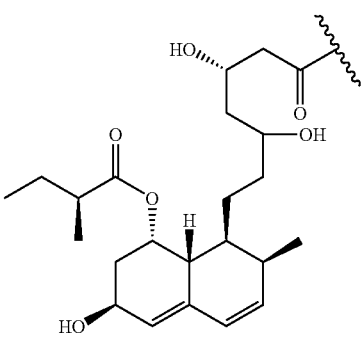 (XXXV)

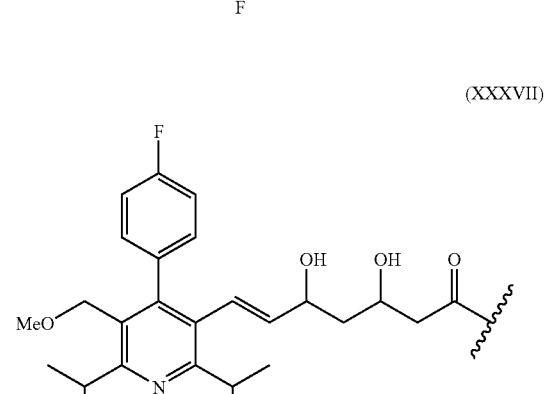 (XXXVI)

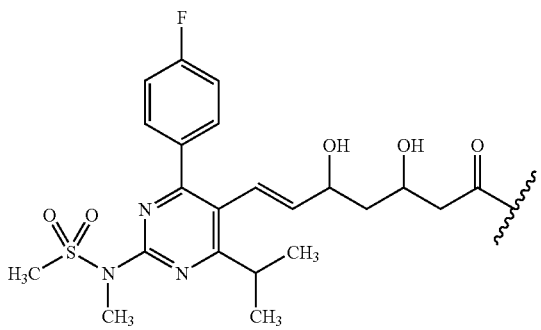 (XXXVII)

(XXXIX)

X is an oxygen atom,

Y is selected from:

straight $C_1$-$C_{10}$ alkylene, b)

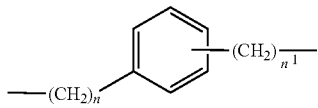

(XXVII)

wherein n is an integer from 0 to 5; and
$n^1$ is an integer from 1 to 5, more preferably $n^1$ is 1;

Another preferred embodiment is the use for the treatment of muscular dystrophies of a nitric oxide-releasing drug selected from the group consisting of:

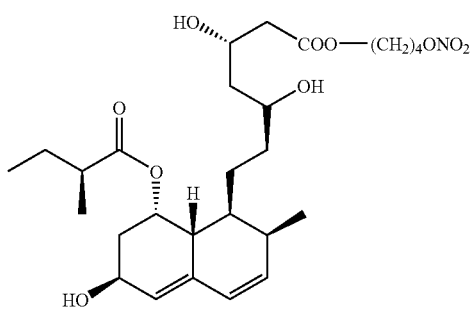

(XXXVb)

which is known as [1S-[1α(βS*,δS*), 2α,6α,8β-(R*), 8aα]]-1,2,6,7,8,8a-hexahydro-β,δ,6-trihydroxy-2-methyl-8-(2-methyl-1-oxobutoxy)-1-naphthaleneheptanoic acid 4-(nitrooxy)butyl ester or as pravastatin 4-(nitrooxy)butyl ester;

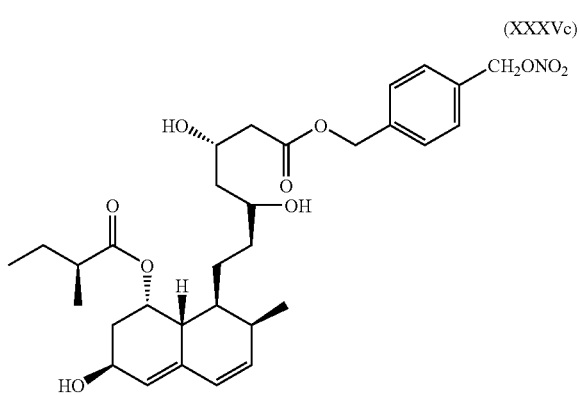

(XXXVc)

which is known as [1S-[1α(βS*,δS*),2α,6α,8β-(R*), 8aα]]-1,2,6,7,8,8a-hexahydro-β,δ,6-trihydroxy-2-methyl-8-(2-methyl-1-oxobutoxy)-1-naphthaleneheptanoic acid 4-(nitrooxymethyl)benzyl ester or as pravastatin 4-(nitrooxymethyl)benzyl ester

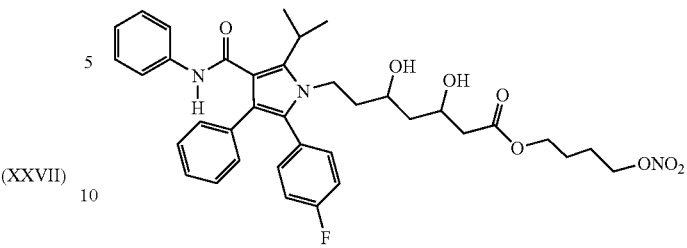

(XXXVIIb)

which is known as (βR,δR)-2(4-fluorophenyl)-β,δ-dihydroxy-5-(1-methylethyl)-3-phenyl-4-[(phenylamino)carbon-yl]-1H-pyrrole-1-heptanoic acid 3-(nitrooxy)butyl ester or as atorvastatin 3-(nitrooxy)butyl ester;

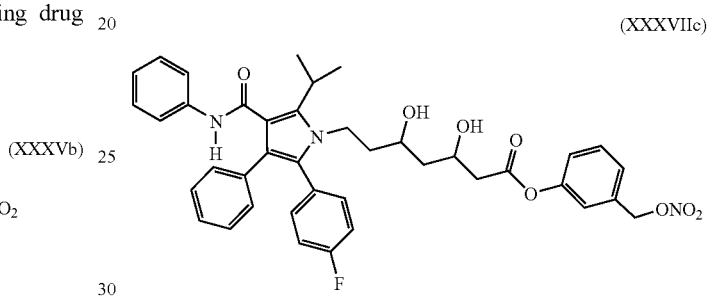

(XXXVIIc)

which is known as (βR,δR)-2(4-fluorophenyl)-β,δ-dihydroxy-5-(1-methylethyl)-3-phenyl-4-[(phenylamino)carbon-yl]-1H-pyrrole-1-heptanoic acid 3-(nitrooxymethyl) benzyl ester or as atorvastatin 3-(nitrooxymethyl)benzyl ester.

The doses to be administered are determined depending upon, for example, age, body weight, symptom, the desired therapeutic effect, the route of administration, and the duration of the treatment. In the human adult, the doses per person at a time are generally from 1 mg to 1000 mg, by oral administration, up to several times per day, and from 1 mg to 100 mg, by parenteral administration (preferably intravenous administration), up to several times per day, or continuous administration for from 1 to 24 hours.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

The general synthesis of the nitric oxide-releasing drug of formula (Ia) wherein M is selected from the residues of formulae (I)-(XXIV) and X are as above defined, is described in the EP 7 559 899

The process of synthesis of 2-(acetyloxy)benzoic acid 3-(nitrooxymethyl)phenyl ester of formula (Ib) is described in EP 1 194 397.

The general synthesis of nitric oxide-releasing of formula (Ia) wherein M is selected from the residues of formulae (XXXIV)-(XXXIX) and the synthesis of pravastatin 4-(nitrooxy)butyl ester are described in WO 2004/105754.

EXAMPLE 1

Muscular dystrophy model ($\alpha$-sarcoglycan-deficient mice). Reference for animal model: Duclos F. et al. J. Cell Biol. 1998 Sep. 21; 142(6):1461-71.
The tested compounds are:
2-acetyloxy benzoic acid 3-(nitrooxymethyl)benzoate of formula (Ib);
pravastatin 4-(nitrooxy)butyl ester which of formula (XXXVb);
2-fluoro-alfa-methyl-4[1,1'-biphenyl]-4-acetic acid 4-nitrooxybutyl ester of formula (IIIb);
prednisolone as reference corticosteroid drug.

Four groups of $\alpha$-sarcoglycan (SG)-null C57BL/6 mice were treated with 2-acetyloxy benzoic acid 3-(nitrooxymethyl) benzoate (compound Ib) (100 mg/kg), pravastatin 4-(nitrooxy)butyl ester (compound XXXVb) (12 mg/kg), 2-fluoro-alfa-methyl-4[1,1'-biphenyl]-4-acetic acid 4-nitrooxybutyl ester (compound IIIb) (30 mg/kg), prednisolone (3 mg/kg) or vehicle, administered daily in the diet.

At indicated time-points (ranging from 20 to 80 days) skeletal muscle function was tested by the free wheel test. 24 hours later animals were sacrificed, tissue isolated and histological characteristics analysed. Infiltrates were assessed after staining with the Azan Mallory technique; Necrotic fibres were measured in hematoxilin-stained sections; creatin kinase was measured using a commercially available kit on blood samples obtained 24 hours prior to the wheel test. (Sampaolesi M., et al Science 301, 487-492, 2003). The data are reported in table 1.

Free wheel running: Voluntary wheel running was used as the exercise paradigm to avoid any physiological changes that may occur due to the stress of forced treadmill running. Mice were housed singly for a 24 hour period in a polycarbonate running wheel equipped with a magnetic counter, the output of which was sent to a speedometer, allowing quantification of the number of revolutions per day. The data are reported in table 2.

Creatine kinase activity measurements: quantitative and kinetic determination of creatine kinase activity in serum of control and drug treated-animals was measured using creatine kinase reagent (Sigma), according to the manufacturer's instructions. Blood was collected from tail of 2-7 months-old mice and serum obtained after centrifugation at 13.000 rpm for 10 minutes was stored at $-80°$ C. before measurements. The data are reported in table 1.

Histology: Diaphragm and tibialis anterior of untreated and drug-treated mice were isolated and included in Killik frozen section medium, quickly frozen and cut into 8-μm thick sections with the muscle fibres oriented transversely using a cryostat. Sections were stained with either Hematoxylin & Eosin or Azan Mallory, to evaluate the number of inflammatory infiltrates and necrotic fibres (18-10 sections for tissue) The data are reported in table 1.

The results show that the tested compounds (Ib), (XXXVb) and (IIIb) were significantly effective in reducing the histological, functional and biochemical alterations which typically occur in these animals. In particular, treated animals showed significantly reduced Inflammatory infiltrates and almost undetectable necrotic fibres. (Table 1)

Plasma levels of creatin kinase, a hallmark of muscle damage, were significantly lower in treated animals; consistently, they performed significantly better on the free-wheel running test. (table 2)

Altogether the data show that the compounds of the present invention have a better profile as compared to prednisolone that is the drug of choice for this pathology.

TABLE 1

| Compound | Days of treat. | Histology data | |
|---|---|---|---|
| | | N° of inflammatory Infiltrates/section | N° of necrotic Fibres/section |
| Control (n = 3) | 80 | 192.6 ± 46.5 | 263.2 ± 43 |
| (XXXVb) (n = 5) | 80 | 54.2 ± 8.05** | 35 ± 2.1** |
| (Ib) (n = 5) | 80 | 91.3 ± 34.5* | 124.1 ± 33** |
| (IIIb) (n = 5) | 80 | 84.2 ± 22.5** | 48.4 ± 2.3** |
| Prednisolone | 80 | 59.4 ± 7.00** | 197.1 ± 23** |

**P < 0.01;
*P < 0.05 vs. control

TABLE 2

| Compound | Days of treatment | CK plasma level (U/ml) | Free wheel test (km/24 h) |
|---|---|---|---|
| Control (n = 3) | 20 | 595.2 ± 87 | 0.34 ± 0.02 |
| | 40 | 892.0 ± 96 | 0.06 ± 0.03 |
| | 60 | 844.3 ± 50 | 0.11 ± 0.02 |
| | 80 | 979.8 ± 91 | 0.14 ± 0.05 |
| (XXXVb) (n = 5) | 20 | 440.6 ± 33** | 0.55 ± 0.03** |
| | 40 | 488.2 ± 96.5* | 0.58 ± 0.01** |
| | 60 | 627.4 ± 69.3** | 0.54 ± 0.03** |
| | 80 | 614.8 ± 37** | 0.65 ± 0.05** |
| (Ib) (n = 5) | 20 | 665.6 ± 51 | 0.65 ± 0.07** |
| | 40 | 944.0 ± 95.5 | 0.42 ± 0.08** |
| | 60 | 444.2 ± 20.2** | 0.31 ± 0.1* |
| | 80 | 494.6 ± 56.1** | |
| (IIIb) (n = 5) | 20 | 662.6 ± 41 | 0.95 ± 0.01** |
| | 40 | 824.0 ± 90.5 | |
| | 60 | 648.2 ± 25.2** | |
| | 80 | 482.3 ± 51.2** | |
| Prednisolone | 20 | 440.6 ± 33** | 0.55 ± 0.01** |
| | 40 | 488.2 ± 96.5* | |
| | 60 | 711.3 ± 69.3** | |
| | 80 | 717.6 ± 31.1** | |

**P < 0.01;
*P < 0.05 vs. control

The invention claimed is:

1. A method of treating muscular dystrophies comprising administering to a subject a nitric oxide releasing compound of formula (Ia)

or enantiomers or diastereoisomers thereof, wherein in the general formula (Ia), M, X and Y have the following meanings:

M is a residue selected from the group consisting of:

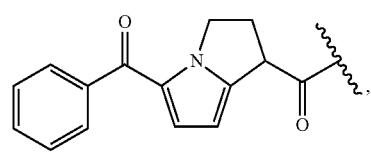

(II)

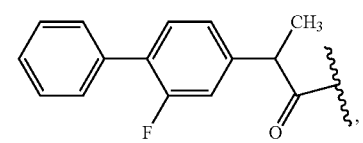

(III)

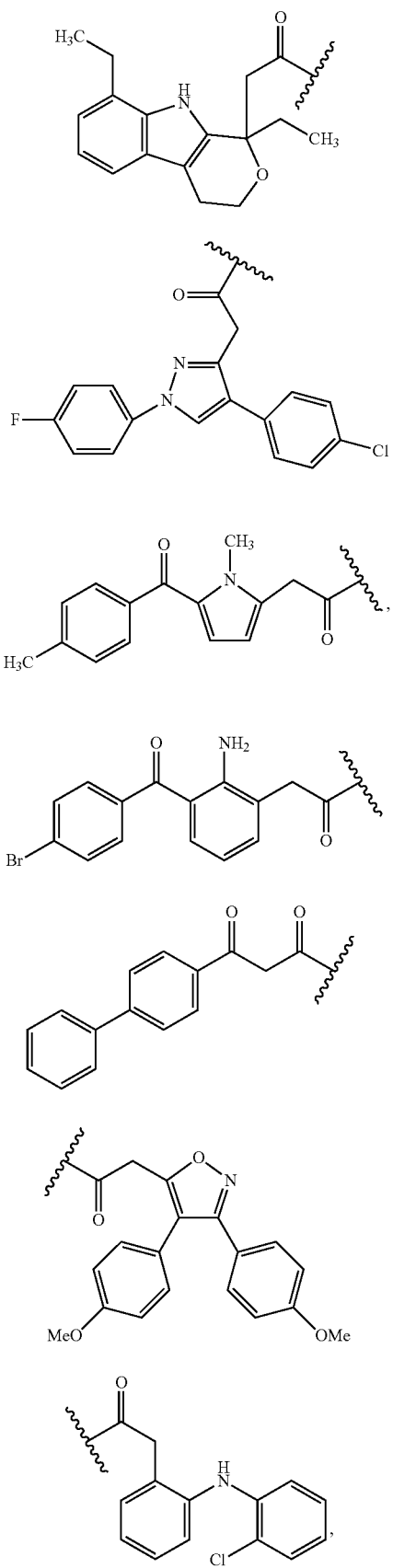
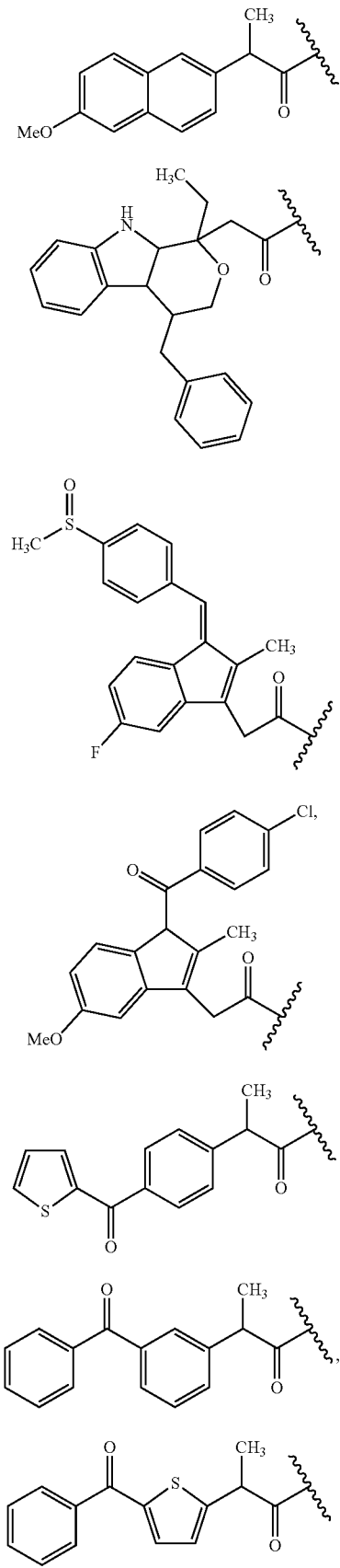

-continued (XVIII)

(XIX)

(XX)

(XXI)

(XXII)

(XXIII)

(XXIV)

(XXV)

(XXVI)

-continued (XXXIV)

(XXXV)

(XXXVI)

(XXXVII)

-continued (XXXIX)

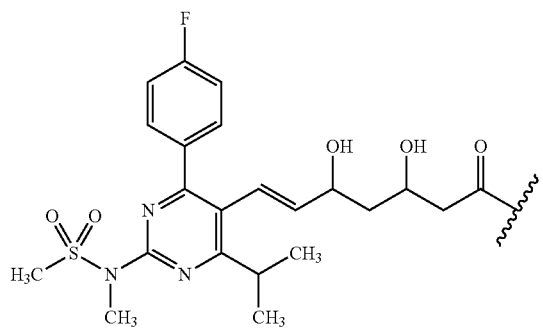

X is —O—, —S— or —NR$^1$—, wherein R$^1$ is H or linear or branched C$_1$-C$_6$ alkyl;

Y is a bivalent radical having the following meanings:

a) —straight or branched C$_1$-C$_{20}$ alkylene being optionally substituted with one or more of the substituents selected from the group consisting of: halogen atoms, hydroxy, —ONO$_2$ and T, wherein T is —OC(O)(C$_1$-C$_{10}$ alkyl)-ONO$_2$ or —O(C$_1$-C$_{10}$ alkyl) ONO$_2$;

C$_5$-C$_7$ cycloalkylene group optionally substituted with linear or branched C$_1$-C$_{10}$ alkyl group;

b)

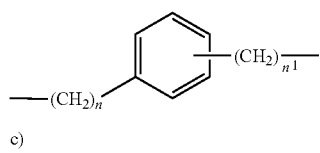
(XXVII)

c)

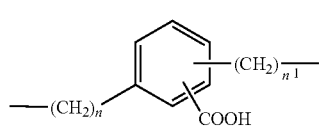
(XXVIII)

wherein n is an integer from 0 to 20;

n$^1$ is an integer from 1 to 20 wherein when Y is selected from the bivalent radicals mentioned under b) and c) then the —ONO$_2$ group of formula is bound to —(CH$_2$)$_n{}^1$;

d)

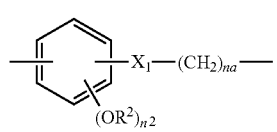
(XXIX)

wherein
X$_1$=—OCO— or —COO— and R$^2$ is H or CH$_3$;
na is an integer from 1 to 20;
n$^2$ is an integer from 0 to 2;

e)

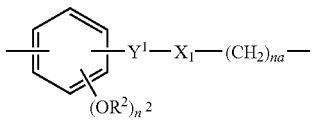
(XXX)

wherein:
Y$^1$ is —CH$_2$—CH$_2$—(CH$_2$)$_n{}^2$—; or —CH=CH—(CH$_2$)$_n{}^2$;
X$_1$, na, n$^2$ and R$^2$ are as defined above;

f)

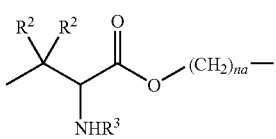
(XXXI)

wherein:
na and R$^2$ are as defined above, R$^3$ is H or —COCH$_3$;
wherein when Y is selected from the bivalent radicals mentioned under d)-f) then the —ONO$_2$ group of formula (I) is bound to —(CH$_2$)$_{na}$;
wherein when X is —NR$^1$—, wherein R$^1$ is as above defined Y cannot be f); and g)

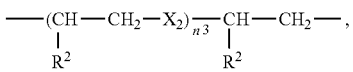
(XXXII)

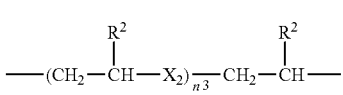
(XXXIII)

wherein
X$_2$ is —O— or —S—;
n$^3$ is an integer from 1 to 6 and
R$^2$ is as defined above.

2. The method of treating muscular dystrophies according to claim 1, wherein the compound of formula (Ia) is 2-fluoro-alfa-methyl-4 [1,1'-biphenyl]-4-acetic acid 4-nitrooxybutyl ester of formula (IIIb)

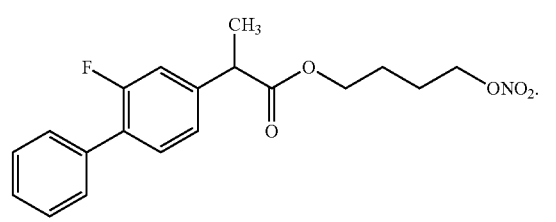
(IIIb)

3. The method of treating muscular dystrophies according to claim 1, wherein in formula (Ia) M is selected from the group consisting of:

(XXXIV)
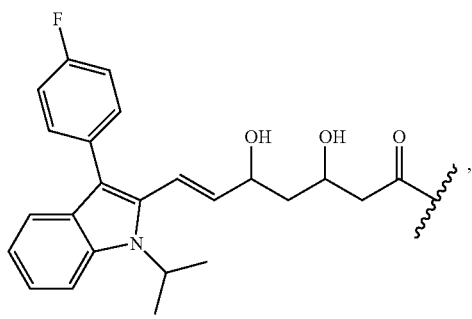
(XXXV)
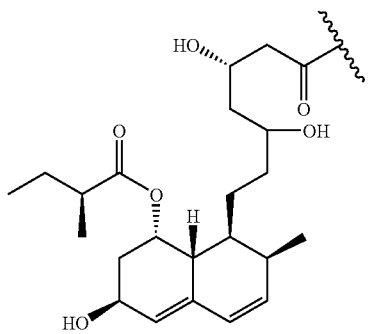
(XXXVI)
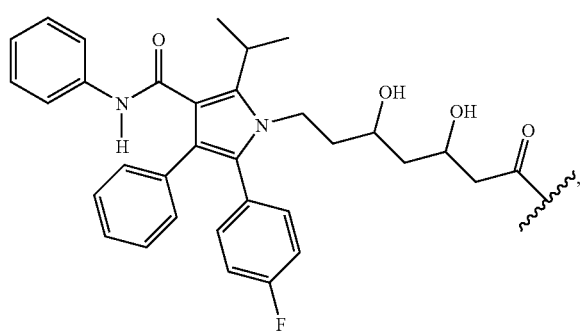
(XXXVII)
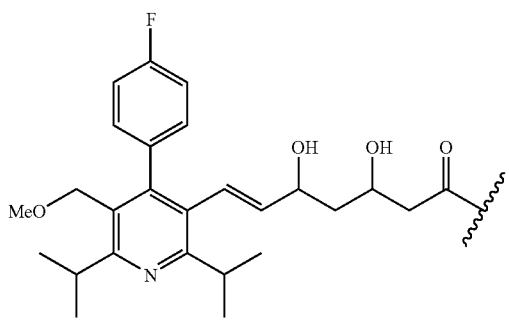
(XXXIX)
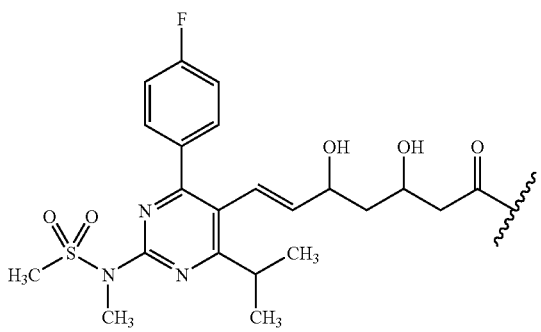
X is an oxygen atom,
Y is selected from:
a)—straight $C_1$-$C_{10}$ alkylene, and
b)
(XXVII)
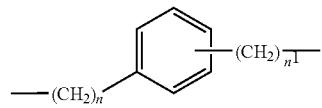
wherein n is an integer from 0 to 5; and
$n^1$ is an integer from 1 to 5.
4. The method of treating muscular dystrophies according to claim 3, wherein the compound of formula (Ia) is selected from the group consisting of:
pravastatin 4-(nitrooxy)butyl ester;
(XXXVb)
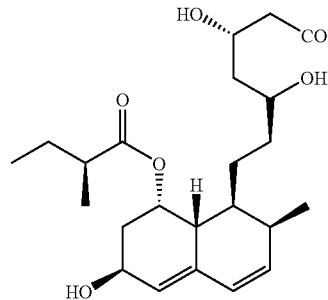

pravastatin 4-(nitro-oxymethyl)benzyl ester

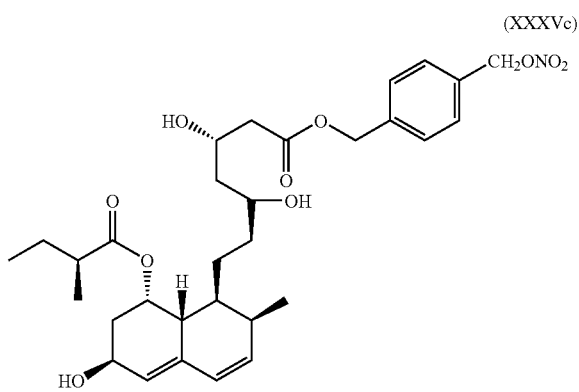

atorvastatin 3-(nitrooxy) butyl ester; and

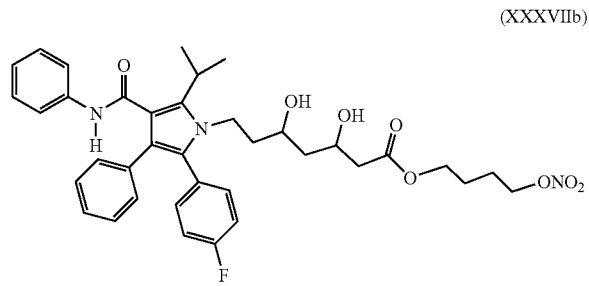

atorvastatin 3-(nitrooxymethyl)benzyl ester

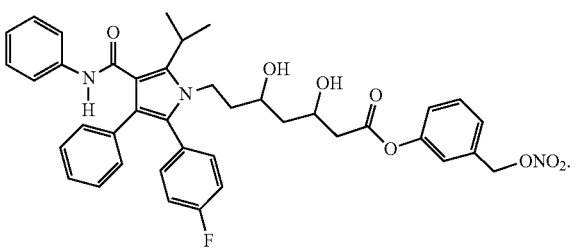

5. The method of treating muscular dystrophies according to claim 1, wherein Y is a straight or branched $C_1$-$C_{10}$ alkylene being optionally substituted with one or more of the substituents selected from the group consisting of: halogen atoms, hydroxy, —$ONO_2$ and T, wherein T is —OC(O) ($C_1$-$C_{10}$ alkyl)-$ONO_2$ or —O($C_1$-$C_{10}$ alkyl)-$ONO_2$.

6. The method of treating muscular dystrophies according to claim 1 wherein Y is a straight or branched $C_1$-$C_{10}$ alkylene.

7. The method of treating muscular dystrophies according to claim 1 wherein Y is a $C_5$-$C_7$ cycloalkylene group optionally substituted with $CH_3$.

8. The method of treating muscular dystrophies according to claim 1 wherein n is an integer from 0 to 5.

9. The method of treating muscular dystrophies according to claim 1 wherein n is 0.

10. The method of treating muscular dystrophies according to claim 1 wherein $n^1$ is an integer from 1 to 5.

11. The method of treating muscular dystrophies according to claim 1 wherein $n^1$ is 1.

12. The method of treating muscular dystrophies according to claim 1 wherein preferably na is an integer from 1 to 5.

13. The method of treating muscular dystrophies according to claim 1, wherein $n^3$ is an integer from 1 to 4.

14. The method of treating muscular dystrophies according to claim 3, wherein $n^1$ is 1.

15. The method of treating muscular dystrophies according to claim 1, wherein an amount of a nitric oxide releasing compound administered to the subject is from 1 mg to 1000 mg.

16. A method of treating muscular dystrophies consisting of administering to a subject a nitric oxide releasing compound of formula (Ia)

M-X—Y—$ONO_2$ (Ia)

or enantiomers or diastereoisomers thereof, wherein in the general formula (Ia), M, X and Y have the following meanings:

M is a residue selected from the group consisting of:

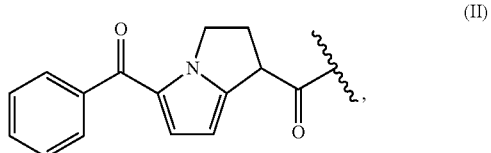
(II)

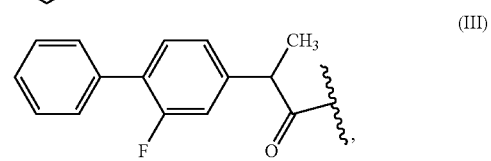
(III)

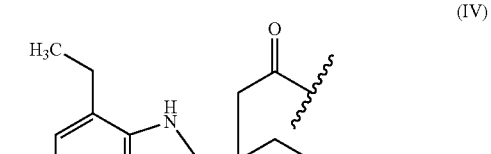
(IV)

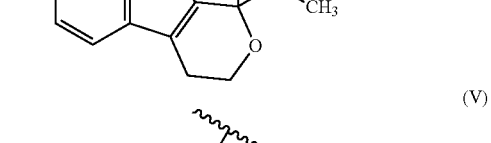
(V)

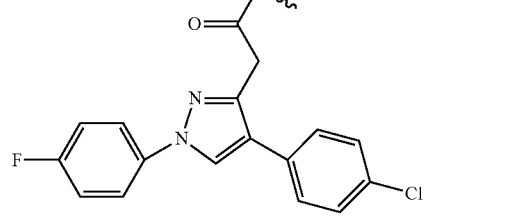
(V)

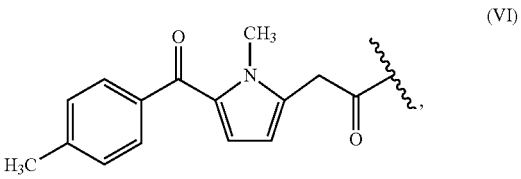
(VI)

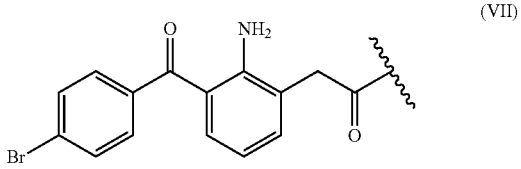
(VII)

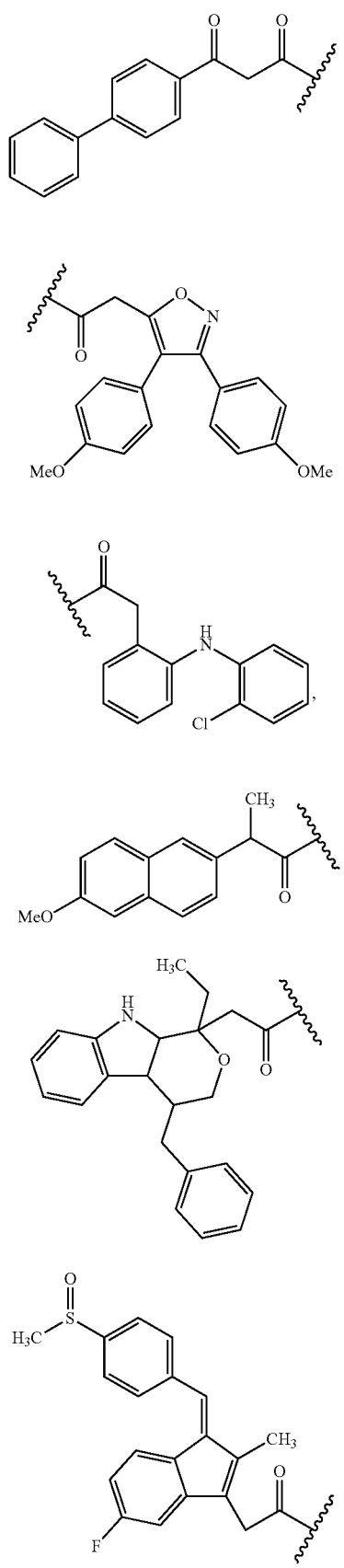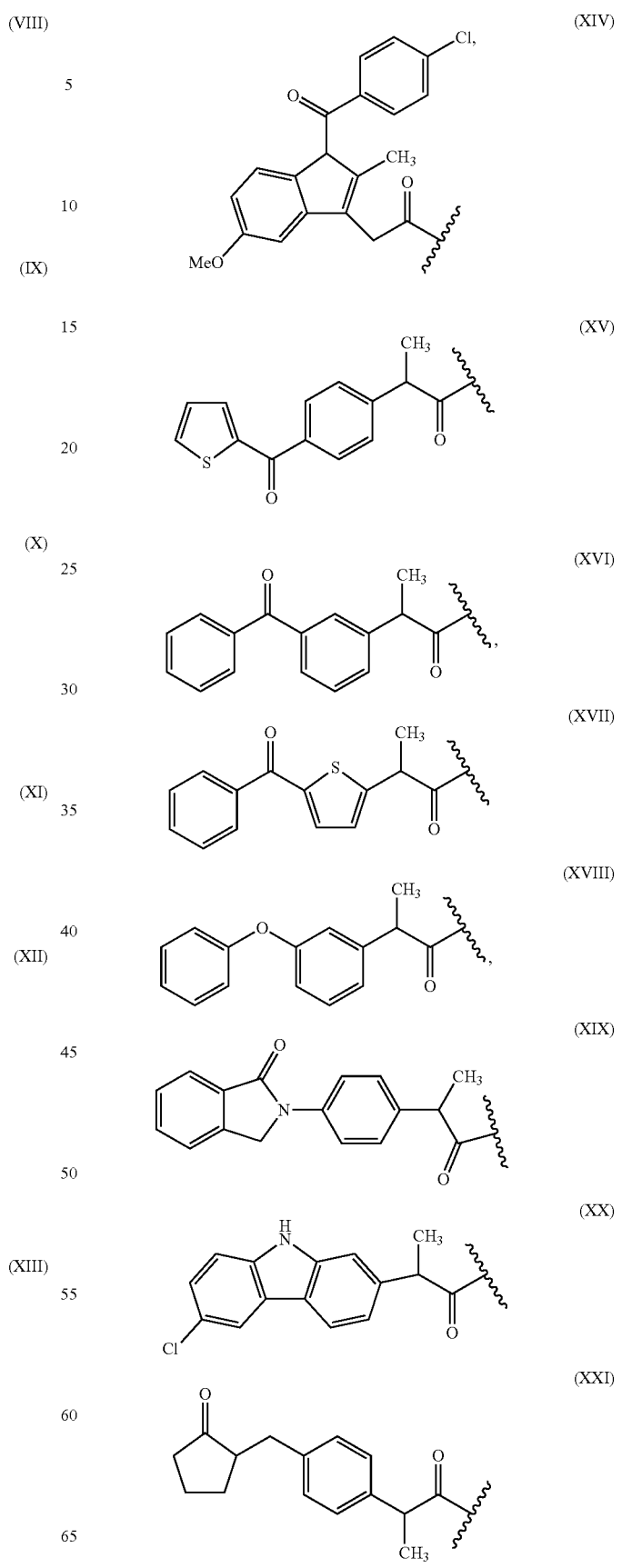

(XXII) 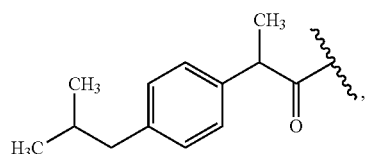

(XXIII) 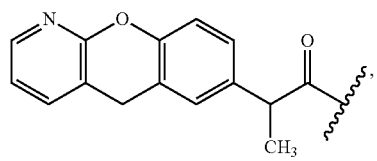

(XXIV) 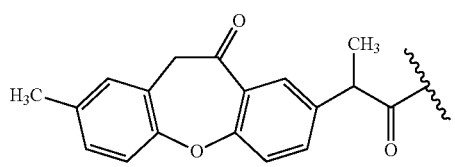

(XXV) 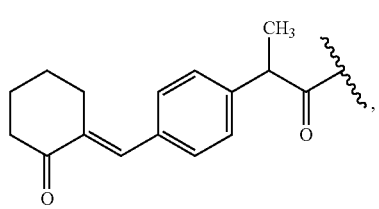

(XXVI) 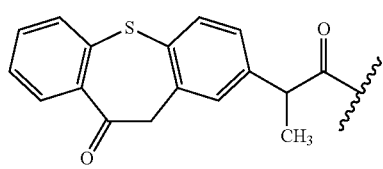

(XXXIV) 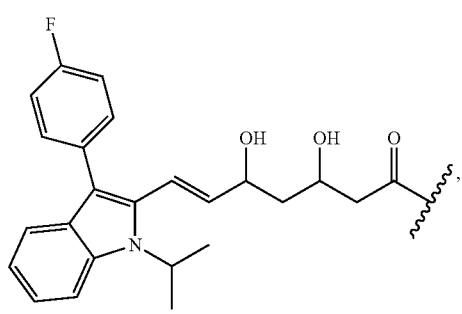

(XXXV) 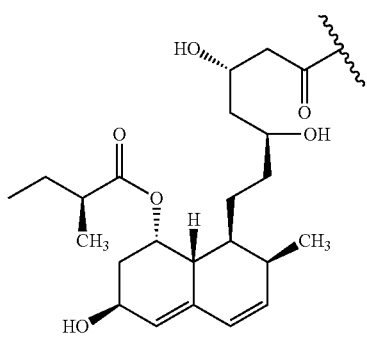

(XXXVI) 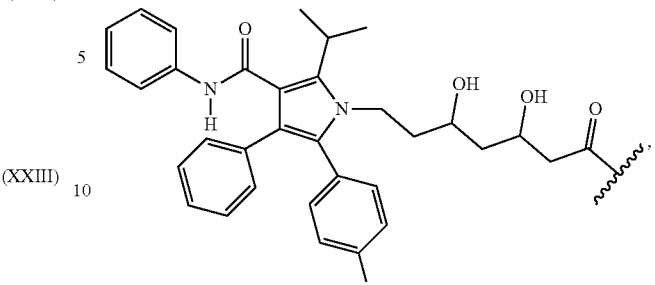

(XXXVII) 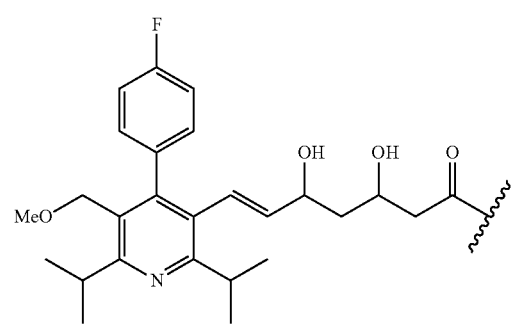

(XXXIX) 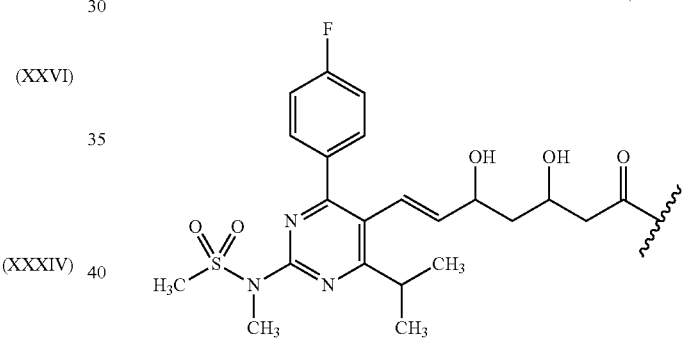

X is —O—, —S— or —NR$^1$—, wherein R$^1$ is H or linear or branched C$_1$-C$_6$ alkyl;

Y is a bivalent radical having the following meanings:

a)—straight or branched C$_1$-C$_{20}$ alkylene being optionally substituted with one or more of the substituents selected from the group consisting of: halogen atoms, hydroxy, —ONO$_2$ and T, wherein T is —OC(O)(C$_1$-C$_{10}$ alkyl)-ONO$_2$ or —O(C$_1$-C$_{10}$ alkyl)ONO$_2$;

C$_5$-C$_7$ cycloalkylene group optionally substituted with linear or branched C$_1$-C$_{10}$ alkyl group;

b)

(XXVII) 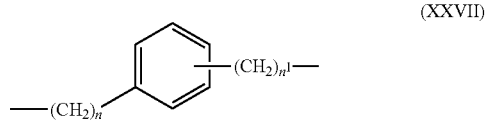

c)

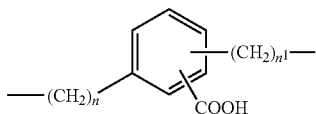
(XXVIII)

wherein n is an integer from 0 to 20;
$n^1$ is an integer from 1 to 20 wherein when Y is selected from the bivalent radicals mentioned under b) and c) then the —ONO$_2$ group of formula is bound to —(CH$_2$)$_{n^1}$—;

d)

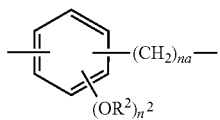
(XXIX)

wherein
$X_1$=—OCO— or —COO— and $R^2$ is H or CH$_3$;
na is an integer from 1 to 20;
$n^2$ is an integer from 0 to 2;

e)

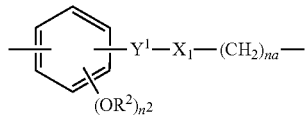
(XXX)

wherein:
$Y^1$ is —CH$_2$—CH$_2$—(CH$_2$)$_{n^2}$—; or —CH=CH—(CH$_2$)$_{n^2}$—;
$X_1$, na, $n^2$ and $R^2$ are as defined above;

f)

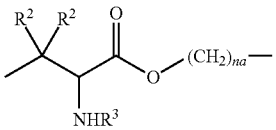
(XXXI)

wherein:
na and $R^2$ are as defined above, $R^3$ is H or —COCH$_3$;
wherein when Y is selected from the bivalent radicals mentioned under d)-f) then the —ONO$_2$ group of formula (I) is bound to —(CH$_2$)$_{na}$;
wherein when X is —NR$^1$, wherein R$^1$ is as above defined Y cannot be f); and g)

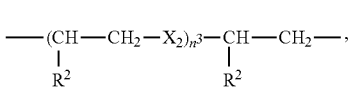
(XXXII)

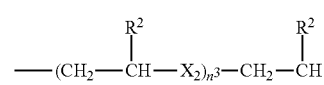
(XXXIII)

wherein
$X_2$ is —O— or —S—;
$n^3$ is an integer from 1 to 6 and
$R^2$ is as defined above.

17. The method of treating muscular dystrophies according to claim 16, wherein the compound of formula (Ia) is 2-fluoro-alfa-methyl-4 [1,1'-biphenyl]-4-acetic acid 4-nitrooxybutyl ester of formula (IIIb)

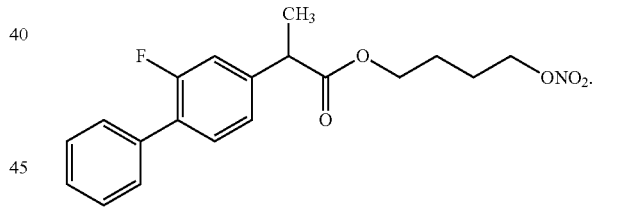
(IIIb)

* * * * *